US00PP14217P29

(12) United States Plant Patent
Bevelander

(10) Patent No.: US PP14,217 P2
(45) Date of Patent: Oct. 7, 2003

(54) HIBISCUS PLANT NAMED 'SAN DIEGO'

(50) Latin Name: *Hibiscus rosa-sinensis*
Varietal Denomination: 'San Diego'

(75) Inventor: Marinus Jacobus Bevelander, Amstelveen (NL)

(73) Assignee: Coöperatieve Vereniging Werkgroep Hibiscus U.A., Rijsenhout (NL)

( * ) Notice: Subject to any disclaimer, the term of this patent is extended or adjusted under 35 U.S.C. 154(b) by 0 days.

(21) Appl. No.: 10/259,933

(22) Filed: Sep. 29, 2002

(51) Int. Cl.[7] ..... A01H 5/00
(52) U.S. Cl. ..... Plt./257
(58) Field of Search ..... Plt./257

*Primary Examiner*—Kent Bell
(74) *Attorney, Agent, or Firm*—C. A. Whealy

(57) ABSTRACT

A new and distinct Hibiscus plant named 'San Diego', characterized by its compact, upright and uniform plant habit that is appropriate for container production; freely branching habit; glossy dark green leaves; freely flowering habit; yellow-colored flowers; and good resistance to flower bud abscission.

1 Drawing Sheet

Botanical classification/cultivar designation: *Hibiscus rosa-sinensis* cultivar 'San Diego'.

BACKGROUND OF THE INVENTION

The present invention relates to a new and distinct cultivar of Hibiscus, botanically known as *Hibiscus rosa-sinensis*, and hereinafter referred to by the name 'San Diego'.

The new Hibiscus is a product of a planned breeding program conducted by the Inventor in Amstelveen, The Netherlands. The objective of the breeding program is to create new compact freely-branching and freely-flowering Hibiscus cultivars appropriate for container production.

The new Hibiscus originated from a cross-pollination made by the Inventor in Amstelveen, The Netherlands, of a proprietary *Hibiscus rosa-sinensis* selection, identified as code number 95.012-9, not patented, as the female, or seed, parent with a proprietary *Hibiscus rosa-sinensis* selection, designated as code number 16.2-91, not patented, as the male, or pollen, parent. The cultivar San Diego was discovered and selected by the Inventor as a flowering plant within the progeny of the stated cross-pollination in a controlled environment in Amstelveen, The Netherlands, in 2000.

Asexual reproduction of the new Hibiscus by vegetative terminal cuttings taken in a controlled environment in Amstelveen, The Netherlands, has shown that the unique features of this new Hibiscus are stable and reproduced true to type in successive generations.

SUMMARY OF THE INVENTION

The cultivar San Diego has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'San Diego'. These characteristics in combination distinguish 'San Diego' as a new and distinct cultivar:

1. Compact, upright and uniform plant habit that is appropriate for container production.

2. Freely branching habit.
3. Glossy dark green leaves.
4. Freely flowering habit.
5. Yellow-colored flowers.
6. Good resistance to flower bud abscission.

Compared to plants of the parents, the proprietary Hibiscus selections code number 95.012-9 and 16.2-91, plants of the new Hibiscus are more upright, more freely branching, and more freely flowering.

Plants of the new Hibiscus can be compared to plants of the Hibiscus cultivar 'Carmen Yellow', not patented. In side-by-side comparisons conducted in Amstelveen, The Netherlands, plants of the new Hibiscus differed from plants of the cultivar Carmen Yellow in the following characteristics:

1. Plants of the new Hibiscus were more freely branching than plants of the cultivar Carmen Yellow.
2. Flower color of plants of the new Hibiscus was darker yellow than flower color of plants of the cultivar Carmen Yellow.

BRIEF DESCRIPTION OF THE PHOTOGRAPH

The accompanying colored photograph illustrates the overall appearance of the new Hibiscus, showing the colors as true as it is reasonably possible to obtain in colored reproductions of this type. Colors in the photograph may differ slightly from the color values cited in the detailed botanical description which accurately describe the colors of the new Hibiscus. The photograph comprises a side perspective view of a typical flowering plant of 'San Diego' grown in a container.

DETAILED BOTANICAL DESCRIPTION

The aforementioned photograph and following observations and measurements describe plants grown in Amstelveen, The Netherlands, grown in 15-cm container in a glass-covered greenhouse during the spring and summer under conditions which closely approximate commercial production. During the production of the plants, day and night temperatures ranged from 15 to 25° C. and light levels were about 500 klux. Plants were about two years old when the photograph and the description were taken. In the description, color references are made to The Royal Horticultural Society Colour Chart, 1995 Edition, except where general terms of ordinary significance are used.

Botanical classification: *Hibiscus rosa-sinensis* cultivar San Diego.

Parentage:

*Female or seed parent.*—Proprietary selection of *Hibiscus rosa-sinensis* designated as code number 95.012-9, not patented.

*Male or pollen parent.*—Proprietary selection of *Hibiscus rosa-sinensis* designated as code number 16.2-91, not patented.

Propagation:

*Type.*—By vegetative terminal cuttings.

*Time to initiate roots.*—About 25 days at a temperature of 23° C.

*Time to produce a rooted young plant.*—About 40 days at a temperature of 22° C.

*Root description.*—Thick; whitish in color.

*Rooting habit.*—Moderately vigorous; freely branching.

Plant description:

*Plant form and growth habit.*—Compact, upright and uniform plant habit; appropriate for container production. Vigorous growth habit.

*Branching habit.*—Freely branching, usually about three or four lateral branches.

*Plant height.*—About 20 to 25 cm.

*Plant diameter* (*area of spread*).—About 40 cm.

*Lateral branch description.*—Length: About 8 cm. Diameter: About 6 mm. Internode length: About 2 cm. Texture: Smooth, glabrous. Color: Close to 146A overlain with 187A.

*Foliage description.*—Arrangement: Alternate, simple. Length: About 5 to 6 cm. Width: About 3 to 4 cm. Shape: Broadly ovate. Apex: Acute. Base: Obtuse. Margin: Irregularly serrate. Texture, upper and lower surfaces: Glabrous; leathery. Venation pattern: Pinnate. Color: Young leaves, upper surface: 146A; glossy. Young leaves, lower surface: Lighter than 146A. Fully expanded leaves, upper surface: Darker than 147A; glossy. Fully expanded leaves, lower surface: 147A. Venation, upper surface: Slightly lighter than 147A. Venation, lower surface: Lighter than 146A. Petiole: Length: About 3 cm. Diameter: About 3 mm. Texture, upper and lower surfaces: Smooth, glabrous. Color, upper and lower surfaces: Darker than 146A.

Flower description:

*Flower arrangement/appearance.*—Rounded flowers arranged singly at terminal leaf axils. Freely flowering with usually about five to six flower buds and/or open flowers per terminal apex. Flowers face mostly upright. Flowers are open for about one day. Flowers persistent. Flowers not fragrant.

*Natural flowering season.*—Usually spring and summer or during periods of warm weather.

*Flower diameter.*—About 10 to 11 cm.

*Flower length* (*height*).—About 3 to 4 cm.

*Flower bud* (*just before showing color*).—Resistance to abscission: Plants of the new Hibiscus have been observed to resist flower bud drop. Length: About 5 cm. Diameter: About 1.5 cm. Shape: Columnar. Color: 146A.

*Petals.*—Arrangement: Corolla consists of five petals that are overlapping towards apex. Length: About 7.5 cm. Width: About 6 cm. Shape: Spatulate or fan-shaped. Apex: Rounded, obtuse. Base: Attenuate. Margin: Entire. Texture, upper and lower surfaces: Smooth, glabrous, satiny. Color: When opening and fully opened, upper surface: 24B. When opening and fully opened, lower surface: 24C. Throat: 187B.

*Sepals.*—Appearance: Five or six sepals fused into a tubular star-shaped calyx. Length: About 1.5 cm. Width: About 5 mm. Shape: Narrowly oblong. Apex: Acute. Base: Fused. Margin: Entire. Texture, upper and lower surfaces: Smooth. Color, upper and lower surfaces: Close to 146A.

*Peduncles.*—Length: About 1.4 cm. Diameter: About 5 mm. Angle: Mostly upright. Strength: Strong, rigid. Texture: Smooth. Color: Lighter than 146A.

*Reproductive organs.*—Androecium: Stamen number: Numerous, about 60 per flower. Anther shape: Globular. Anther length: About 1 mm. Anther color: 12A. Amount of pollen: Abundant. Pollen color: Close to 15A. Gynoecium: Pistil number: One per flower. Pistil length: About 8 to 9 cm. Style length: About 8 cm. Style texture: Smooth, waxy. Style color: 16B. Stigma appearance: Five, rounded. Stigma color: 24B. Ovary color: Close to 154C to 154D.

*Fruit/seed.*—Fruit and seed production has not been observed.

Disease/pest resistance: Plants of the new Hibiscus have not been observed to be resistant to pathogens and pests common to Hibiscus.

It is claimed:

1. A new and distinct Hibiscus plant named 'San Diego', as illustrated and described.

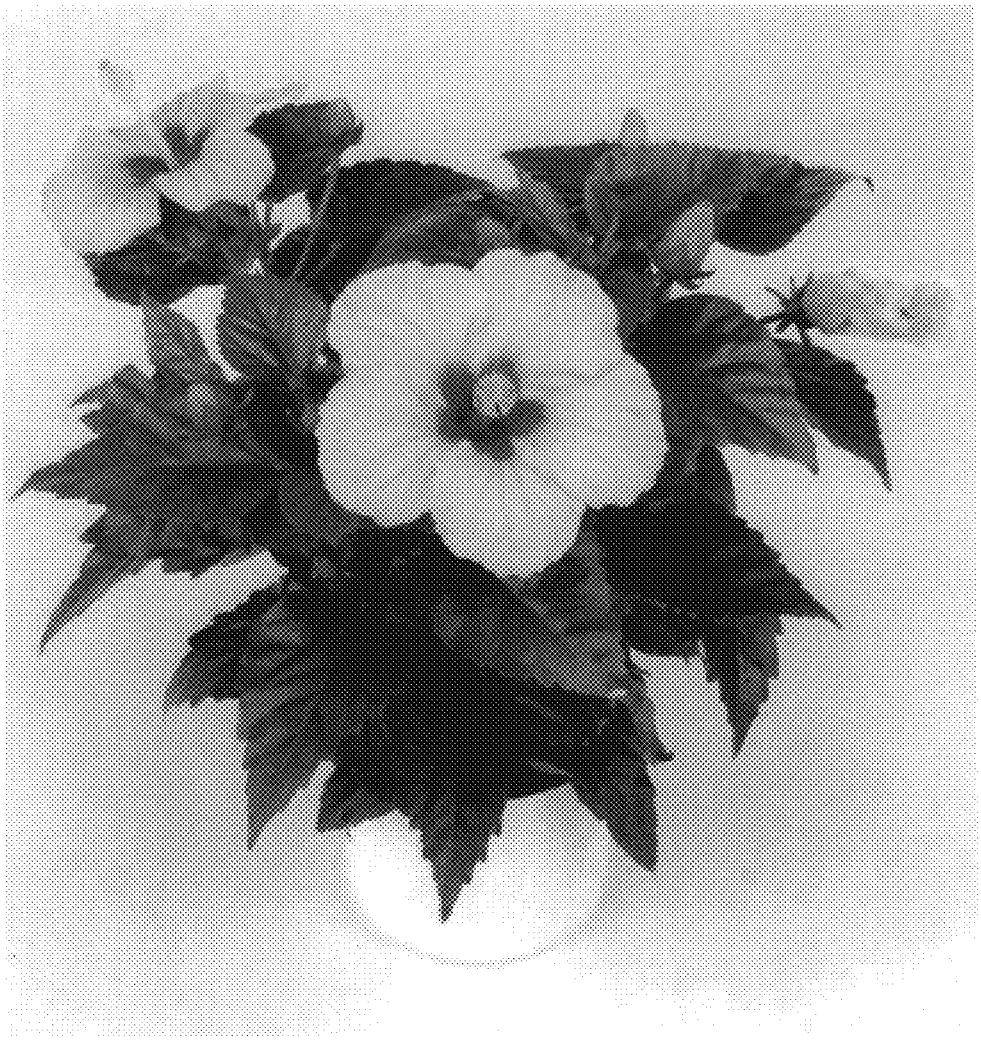

* * * * *